United States Patent
Fink et al.

(10) Patent No.: US 8,260,428 B2
(45) Date of Patent: Sep. 4, 2012

(54) METHOD AND SYSTEM FOR TRAINING A VISUAL PROSTHESIS

(75) Inventors: Wolfgang Fink, Montrose, CA (US); Mark A. Tarbell, Walnut, CA (US)

(73) Assignee: California Institute of Technology, Pasadena, CA (US)

( * ) Notice: Subject to any disclaimer, the term of this patent is extended or adjusted under 35 U.S.C. 154(b) by 1160 days.

(21) Appl. No.: 12/041,203

(22) Filed: Mar. 3, 2008

(65) Prior Publication Data

US 2008/0228242 A1    Sep. 18, 2008

Related U.S. Application Data

(63) Continuation-in-part of application No. 12/016,539, filed on Jan. 18, 2008, which is a continuation of application No. 10/837,163, filed on Apr. 30, 2004, now Pat. No. 7,321,796.

(60) Provisional application No. 60/904,573, filed on Mar. 1, 2007, provisional application No. 60/994,097, filed on Sep. 17, 2007, provisional application No. 60/467,037, filed on May 1, 2003.

(51) Int. Cl.
*A61N 1/36* (2006.01)
(52) U.S. Cl. .......................................... 607/54
(58) Field of Classification Search ............ 607/53, 607/54
See application file for complete search history.

(56) References Cited

U.S. PATENT DOCUMENTS

| | | |
|---|---|---|
| 5,016,633 A | 5/1991 | Chow |
| 5,024,223 A | 6/1991 | Chow |
| 5,109,844 A | 5/1992 | de Juan, Jr. et al. |
| 5,476,494 A | 12/1995 | Edell et al. |
| 5,556,423 A | 9/1996 | Chow et al. |
| 5,575,813 A | 11/1996 | Edell et al. |
| 5,597,381 A | 1/1997 | Rizzo, III |
| 5,767,913 A | 6/1998 | Kassatly |
| 5,790,177 A | 8/1998 | Kassatly |
| 5,836,996 A | 11/1998 | Doorish |
| 5,865,839 A | 2/1999 | Doorish |
| 5,873,901 A | 2/1999 | Wu et al. |
| 5,895,415 A | 4/1999 | Chow et al. |
| 5,935,155 A | 8/1999 | Humayun et al. |
| 5,944,747 A | 8/1999 | Greenberg et al. |
| 6,055,048 A * | 4/2000 | Langevin et al. .......... 356/237.1 |
| 6,165,192 A | 12/2000 | Greenberg et al. |
| 6,230,857 B1 | 5/2001 | Ciriello |
| 6,278,441 B1 * | 8/2001 | Gouzman et al. ............. 345/163 |
| 6,324,429 B1 | 11/2001 | Shire et al. |
| 6,389,317 B1 | 5/2002 | Chow et al. |

(Continued)

OTHER PUBLICATIONS

Napp-Zinn et al. "Recognition and Tracking of Event Patterns with Delay-Adaption in Biology-Inspired Pulse Processing Neural Net (BPN) Hardware," Biological Cybernetics, Jun. 1, 1993.

(Continued)

*Primary Examiner* — George Evanisko
(74) *Attorney, Agent, or Firm* — Ropes & Gray LLP (57) ABSTRACT

A method for training a visual prosthesis includes presenting a non-visual reference stimulus corresponding to a reference image to a visual prosthesis patient. Training data sets are generated by presenting a series of stimulation patterns to the patient through the visual prosthesis. Each stimulation pattern in the series is determined at least in part on a received user perception input and a fitness function optimization algorithm. The presented stimulation patterns and the user perception inputs are stored and presented to a neural network off-line to determine a vision solution.

34 Claims, 8 Drawing Sheets

U.S. PATENT DOCUMENTS

| | | |
|---|---|---|
| 6,393,327 B1 | 5/2002 | Scribner |
| 6,400,989 B1 * | 6/2002 | Eckmiller ........................ 607/54 |
| 6,430,450 B1 * | 8/2002 | Bach-y-Rita et al. ......... 607/134 |
| 6,458,157 B1 | 10/2002 | Suaning et al. |
| 6,493,587 B1 | 12/2002 | Eckmiller et al. |
| 6,493,878 B1 | 12/2002 | Kassatly |
| 6,507,758 B1 | 1/2003 | Greenberg et al. |
| 6,530,954 B1 | 3/2003 | Eckmiller |
| 6,533,798 B2 | 3/2003 | Greenberg et al. |
| 6,611,716 B2 | 8/2003 | Chow et al. |
| 6,647,297 B2 | 11/2003 | Scribner |
| 6,668,190 B2 | 12/2003 | Iezzi et al. |
| 2001/0037061 A1 | 11/2001 | Eckmiller et al. |
| 2002/0002381 A1 | 1/2002 | Greenberg et al. |
| 2002/0038134 A1 | 3/2002 | Greenberg et al. |
| 2002/0087202 A1 | 7/2002 | Chow et al. |
| 2002/0091421 A1 | 7/2002 | Greenberg et al. |
| 2002/0091422 A1 | 7/2002 | Greenberg |
| 2002/0099420 A1 | 7/2002 | Chow et al. |
| 2002/0111655 A1 | 8/2002 | Scribner |
| 2002/0161417 A1 | 10/2002 | Scribner |
| 2002/0193845 A1 | 12/2002 | Greenberg et al. |
| 2003/0004546 A1 | 1/2003 | Casey |
| 2003/0014089 A1 | 1/2003 | Chow et al. |
| 2003/0028225 A1 | 2/2003 | Chow et al. |
| 2003/0055494 A1 | 3/2003 | Bezuidenhout et al. |
| 2003/0093132 A1 | 5/2003 | Eckmiller |
| 2003/0097165 A1 | 5/2003 | Krulevitch |
| 2003/0097166 A1 | 5/2003 | Krulevitch |
| 2003/0122954 A1 | 7/2003 | Kassatly |
| 2003/0158588 A1 | 8/2003 | Rizzo et al. |
| 2003/0181957 A1 | 9/2003 | Greenberg et al. |
| 2004/0030383 A1 * | 2/2004 | Havey et al. ................... 623/4.1 |
| 2004/0039401 A1 | 2/2004 | Chow et al. |

OTHER PUBLICATIONS

Becker et al. Psychophysical Test of a Tunable Retina Encoder for Retina Implants. IEEE, p. 192-95. (1999).

* cited by examiner

METHOD AND SYSTEM FOR TRAINING A VISUAL PROSTHESIS

CROSS REFERENCE TO RELATED APPLICATIONS

This application is a continuation-in-part of U.S. patent application Ser. No. 12/016,539, entitled "Method and System for Training a Visual Prosthesis" filed on Jan. 18, 2008, which is a continuation of U.S. patent application Ser. No. 10/837,163, entitled "Method and System for Training a Visual Prosthesis" filed on Apr. 30, 2004, which claims priority to U.S. Provisional Patent Application No. 60/467,037, entitled "Blind Patient in the Loop Optimization Algorithm for Electrical Stimulation Patterns for Retinal Implants Electrode Arrays" filed on May 1, 2003. This application claims priority to U.S. Provisional Patent Application No. 60/904, 573, entitled "Tactile Feedback Device for Visually Impaired or Blind People" filed on Mar. 1, 2007 and U.S. Provisional Patent Application No. 60/994,097, entitled "Tactile Feedback Device for Visually Impaired or Blind People" filed on Sep. 17, 2007. All these prior applications are hereby incorporated by reference in their entireties.

GOVERNMENT CONTRACT

The U.S. Government has a paid-up license in this invention and the right in limited circumstances to require the patent owner to license others on reasonable terms as provided for by the terms of Grant No. DE-FG02-06ER64310/ T-103506 awarded by DOE.

FIELD OF INVENTION

The invention relates generally to sensory prosthesis technology, and in one embodiment, to methods for training visual prostheses.

BACKGROUND OF THE INVENTION

A healthy individual's visual perception process begins with the individual's retina(s) receiving stimulation in the form of light. The individual's nerve cells within the retina communicate a signal corresponding to the stimulation to the optic nerve. The optic nerve subsequently transmits a corresponding signal to the visual cortex through the lateral geniculate nucleus. For a vision impaired patient, visual perception may be induced by providing electrical stimulation at one or more of these locations, depending on the nature of the patient's given impairment.

Previous studies have shown that controlled electrical stimulation of the retina induces visual perception in blind patients. A healthy retina has over 100 million photoreceptors. Far fewer, however, are required to restore at least low resolution vision in blind individuals. For example, to enable a blind person to attain unaided mobility and large print reading, two important quality of life indicators, tests have shown that such abilities can be provided. Implants, such as those developed by Second Sight, LLP of Sylmar, Calif., or described, for example, in U.S. Pat. No. 5,935,155 by Humayun et al. and U.S. Pat. No. 5,109,844 to De Juan, Jr. et al., which include arrays of electrodes coupled to nerve cells of a patient's retina, have been shown to be able to restore low resolution visual perception to blind patients.

Other groups have explored simulating sensory perception using tactile and electrical stimulation of sensations outside of the typical visual pathways. For example, a group at the University of Wisconsin has developed an electrode array for electrically stimulating a patient's tongue to generate visual perceptions. Others, for example, at the University of Arizona, Tuscon have explored inducing visual perceptions through tactile stimulation of the skin.

While current implant technology has been demonstrated to stimulate some amount of visual perception, each visual prosthesis needs to be trained for its individual patient in order to effectively elicit the appropriate visual perception. Prime candidates for visual prostheses are previously sighted individuals who have had their normal visual nerve activity damaged by various conditions, for example macular degeneration or retinitis pigmentosa. However, due to the visual damage in such candidates, predicting in advance the perception induced by a visual prosthesis in a particular candidate has proven difficult.

SUMMARY OF THE INVENTION

The invention addresses the deficiencies in the art by, in one aspect, providing systems and methods for training a sensory prosthesis (e.g., a visual prosthesis such as a retinal implant, a cortical implant, a lateral geniculate nucleus implant, a tongue stimulator, a mechanical body stimulator, an electrical body stimulator, or an optical nerve implant) to adapt to the patient in which it is implanted. According to this aspect, the method includes providing a non-visual reference stimulus to a patient having a visual prosthesis based on a reference image. The non-visual reference stimulus is intended to provide the patient an expectation of the visual image the visual prosthesis will induce. Non-visual reference stimuli include, without limitation, a pinboard, Braille text, or a verbal communication. The visual prosthesis stimulates the patient's nerve cells with a series of stimulus patterns attempting to induce a visual perception that matches the patient's expected perception derived from the non-visual reference stimulus. The patient provides feedback to indicate which of the series of stimulus patterns induces a perception that most closely resembles the expected perception. The invention employs the patient feedback as a fitness function (also referred to as a cost function or an energy function). Subsequent stimuli provided to the patient through the visual prosthesis are based, at least in part, on the previous feedback of the patient as to which stimulus pattern(s) induce the perception that best matches the expected perception. According to one embodiment, the subsequent stimulus patterns are also based, at least in part, on a fitness function optimization algorithm. In one embodiment, the fitness function optimization algorithm is a simulated annealing algorithm. In another implementation, the fitness function optimization algorithm is a genetic algorithm. In another embodiment, the fitness function optimization algorithm is an evolutionary algorithm, an evolutionary strategy, or other fitness function optimization algorithms known to those skilled in the art.

According to one feature, the invention stores the reference image and the series of stimulus patterns presented to the patient, along with the choices indicated by the patient, as a first training set. The invention may generate additional training sets using additional reference images and series of corresponding stimulus patterns. In one embodiment, the fitness function optimization algorithm is modified between the stimulation of each series of stimulation patterns. In other embodiments, the fitness function optimization algorithm is static. According to one feature, a neural network analyzes the training set offline to determine a vision solution for the visual prosthesis.

In another aspect, the invention provides a system for training a sensory prosthesis (e.g., a visual prosthesis such as a retinal implant, a cortical implant, a lateral geniculate nucleus implant, a tongue stimulator, a mechanical body stimulator, an electrical body stimulator, or an optical nerve implant). The system includes a training processor configured to generate and present series of stimulation patterns corresponding to a reference image. As in the above-described method, subsequent stimulation patterns are based, at least in part, on patient input and/or a fitness function optimization algorithm.

The system includes a tool for presenting to a patient the reference image that the patient should expect to perceive using a non-visual reference stimulus. The reference image presentation tool includes an array of mechanical projections for presenting a non-visual representation of the reference image, a plurality of actuators for adjusting the positions of the mechanical projections with respect to a surface, an input for receiving projection position instructions, and a controller for controlling the plurality of actuators based on the received projection position instructions. The system includes a user input for the patient to present a perception of a stimulation pattern. The user input includes an array of mechanical projections that a user can manually move, a plurality of position sensors for determining the positions of the mechanical projections with respect to a surface, and a processor for outputting user perception inputs based on the positions of the mechanical projections.

BRIEF DESCRIPTION OF THE FIGURES

The foregoing discussion will be understood more readily from the following detailed description of the invention with reference to the following drawings.

ILLUSTRATIVE DESCRIPTION

For illustrative purposes, the methods and systems below are described with specific reference to retinal implants. The methods also apply to the training of sensory prostheses (e.g., visual prosthesis such as optical nerve implants, lateral geniculate nucleus implants, tongue stimulators, mechanical body stimulators, electrical body stimulators, and cortical implants). In the present invention, a visual prosthesis induces visual perception or its equivalent in a patient by conveying spatial information to the patient using any suitable means.

Figure 1:
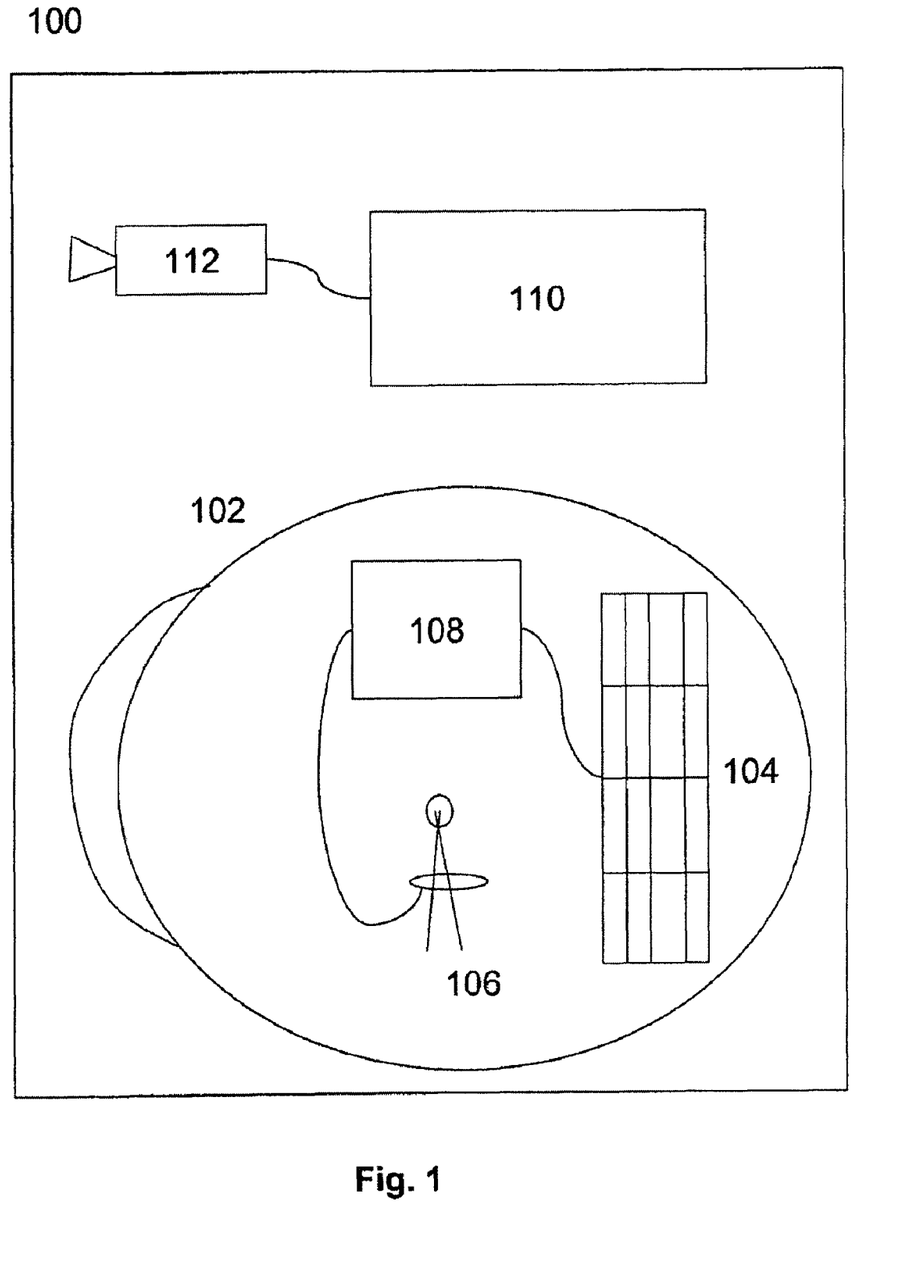
FIG. 1 is a schematic depiction of a retinal implant according to an illustrative embodiment of the invention.

FIG. 1 is a schematic depiction of a retinal implant system 100 according to one embodiment of the invention. The retinal implant system 100 includes elements implanted within a patient's eye 102 and portions exterior to the patient's eye 102. For example, in the illustrative example, the retinal implant system 100 includes an electrode array 104, a receiver 106, and an electrode array processor 108 implanted within the patient's eye 102. An image processor 110 and video camera 112 remain outside of the patient's eye. In other embodiments, the video camera 112 and/or the image processor 110 can be implanted within the patient's eye 102 or elsewhere within the patient. In other embodiments, the video camera 112 can be replaced with other image capture devices such as CCD arrays.

The electrode array processor 108 is electrically connected to the electrode array 104 and generates an electrical stimulus for output through each electrode in the electrode array 104. Electrode stimulation does not necessarily have a one-to-one correspondence to a patient perceiving a pixel of light. For example, in some patients, in order to induce perception of one particular pixel of vision, two or more electrodes may need to be energized. The electrode array processor 108 receives its drive instructions from the receiver 106, which in turn wirelessly receives instructions from the image processor 110.

In the illustrative embodiment, the patient wears the image processor 110, for example, on his or her belt. In addition to the image processor 110, the retinal implant system 100 includes a camera 112 for providing vision information to the image processor 110. The image processor 110 then processes the vision information to determine the appropriate electrical stimulus patterns for the retinal implant 100. The image processor 110 can be implemented in either hardware, such as, and without limitation, an ASIC, Digital Signal Processor, or other integrated circuit, or in software operating on a computing device, or in a combination of the two.

In one embodiment, the image processor 110 receives a digital image from the video camera 112. The image processor 110 converts the received image to a gray scale and reduces/downscales the resolution of the image to a resolution matching the number of electrodes in the electrode array 104. In other embodiments, the image processor 110 retains the image in color. The image processor 110 then determines the appropriate electrical stimulus for each electrode in the electrode array 104 based on a vision solution. The vision solution determines the values of a number of parameters that can be manipulated for each electrode, including, without limitation, for example, the amplitude of the voltage applied to each electrode (if any), the timing of the onset of the electrical signal applied to each electrode relative to the other electrodes, the shape of the signal applied to each electrode, the width of a pulse applied to the electrode, the frequency of the signal applied, and the duration of the voltage applied to the electrode. In contrast to methods of training optical implants that tune temporal-spatial filters to mimic retinal function, the illustrative training method determines direct electrode outputs in response to received images.

The image processor 110, after generating a stimulus pattern for the electrode array 104, transmits the stimulus pattern wirelessly to the receiver 106 within the patient's eye 102.

Figure 2:
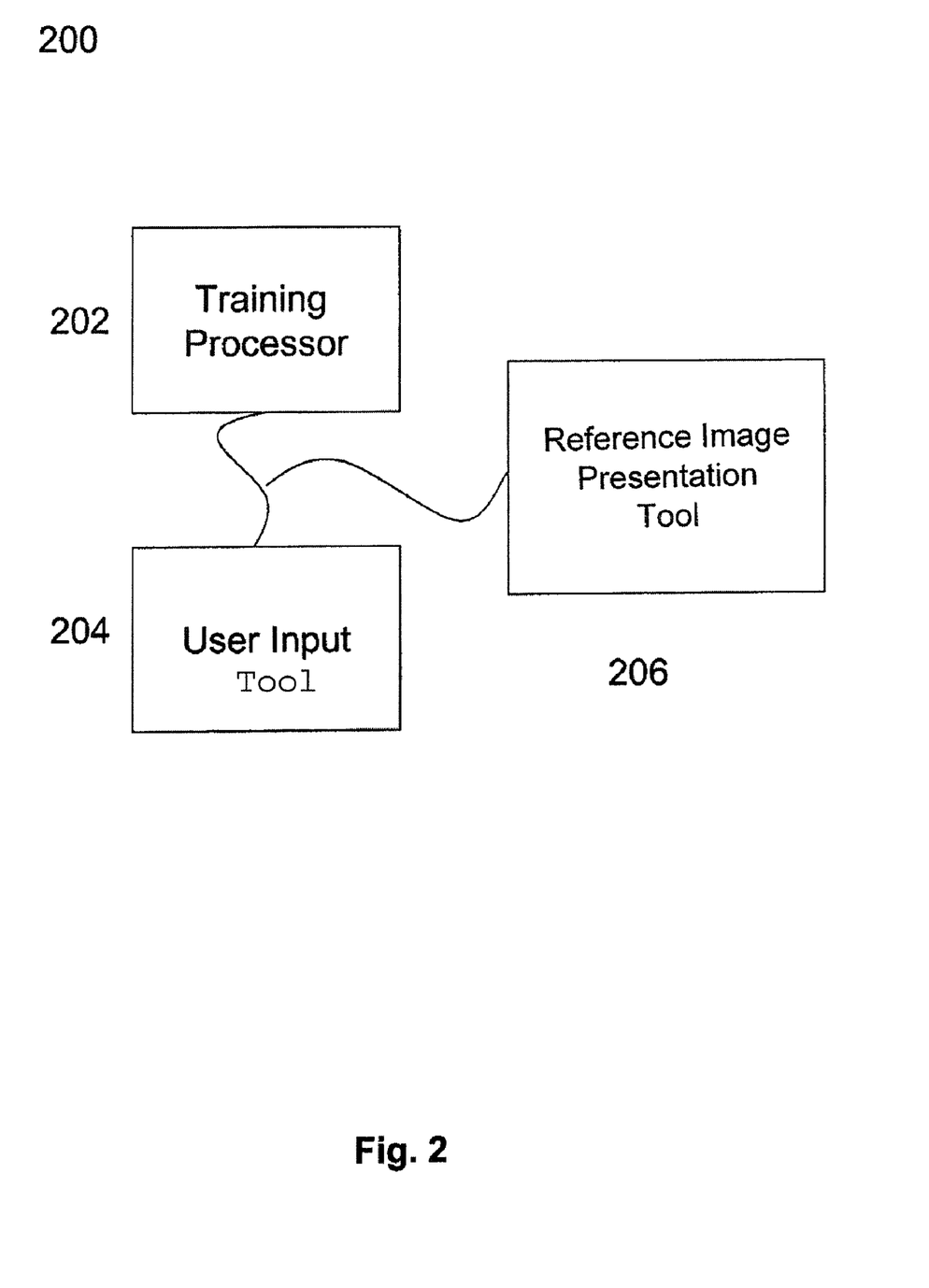
FIG. 2 is a block diagram of a system for retinal implant training according to an illustrative embodiment of the invention.

FIG. 2 is a conceptual high-level block diagram of a retinal implant training system 200. The training system 200 includes a training processor 202, a user input tool 204, and a reference image presentation tool 206. The elements of the training system 200 will be best understood with reference to the method described in FIG. 3.

Figure 3:
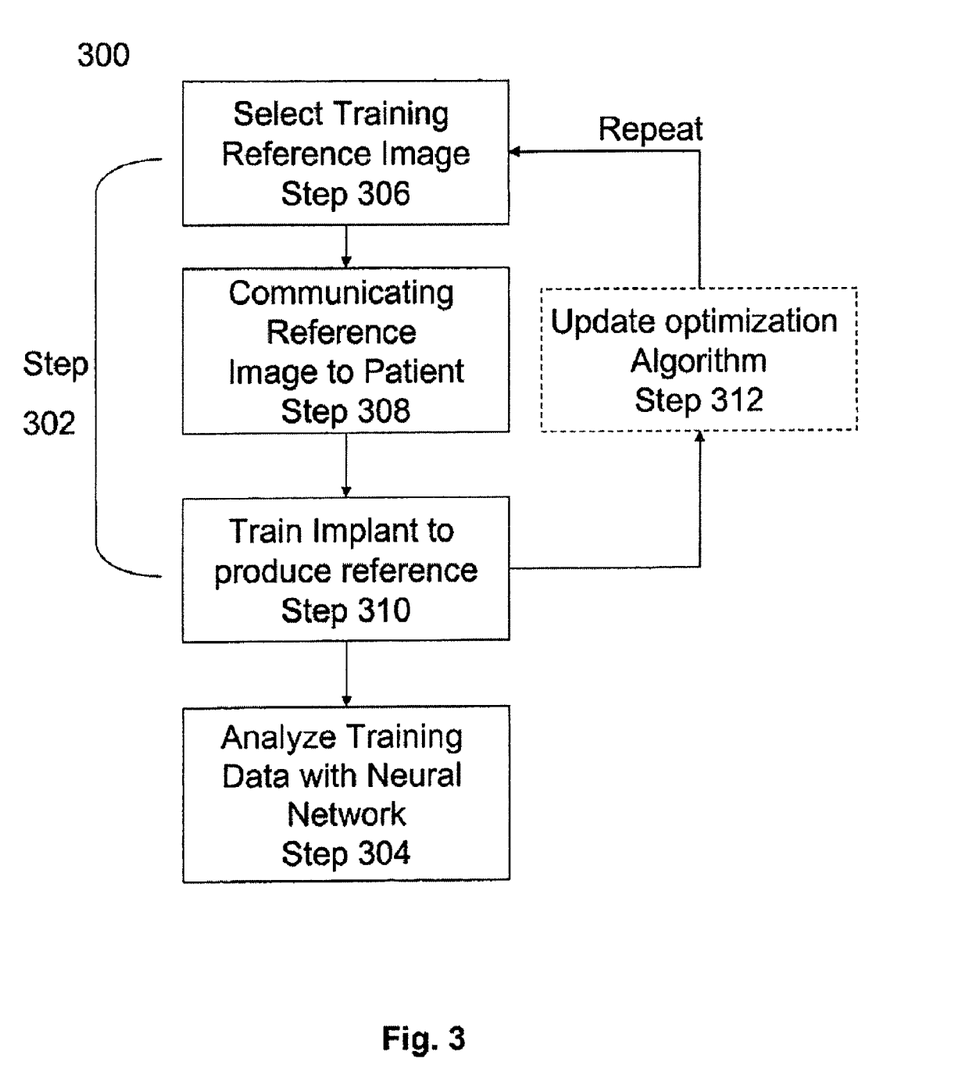
FIG. 3 is a flowchart of a method of training a retinal implant according to an illustrative embodiment of the invention.

FIG. 3 is a flowchart of a method 300 for training a retinal implant 100, such as the implant described in FIG. 1, to determine a vision solution for an individual patient's retinal implant 100. A patient participates in training his or her individual implant 100 with the aid of the training system 200. In general, the training method 300 can be divided into two portions, generating training data (step 302) and processing training data (step 304) to produce the vision solution.

Generating training data (step 302) can be further divided into three processes: i) selecting a training reference image (step 306), ii) communicating the reference image to the patient (step 308), and iii) training the patient's implant to successfully produce the reference image (step 310).

First, the training processor 202 selects a first training reference image (step 306) to attempt to stimulate perception of that image in the patient. In one embodiment the training reference image is selected from a predefined group, such as letters, numbers, or basic shapes. For example, the first training reference image may be a solid white rectangle. Subsequent training reference images include individual straight vertical and horizontal lines at the extremities of the patient's inducible field-of-view. Other preliminary training reference images include individual bright spots at various locations in a patient's field of view. The training set then identifies the first training reference image to the patient using a non-visual reference stimulus (step 308), for example by employing the reference image presentation tool 206. The non-visual reference stimulus provides the patient an expectation of the perception the implant 100 is attempting to induce.

Figure 4:
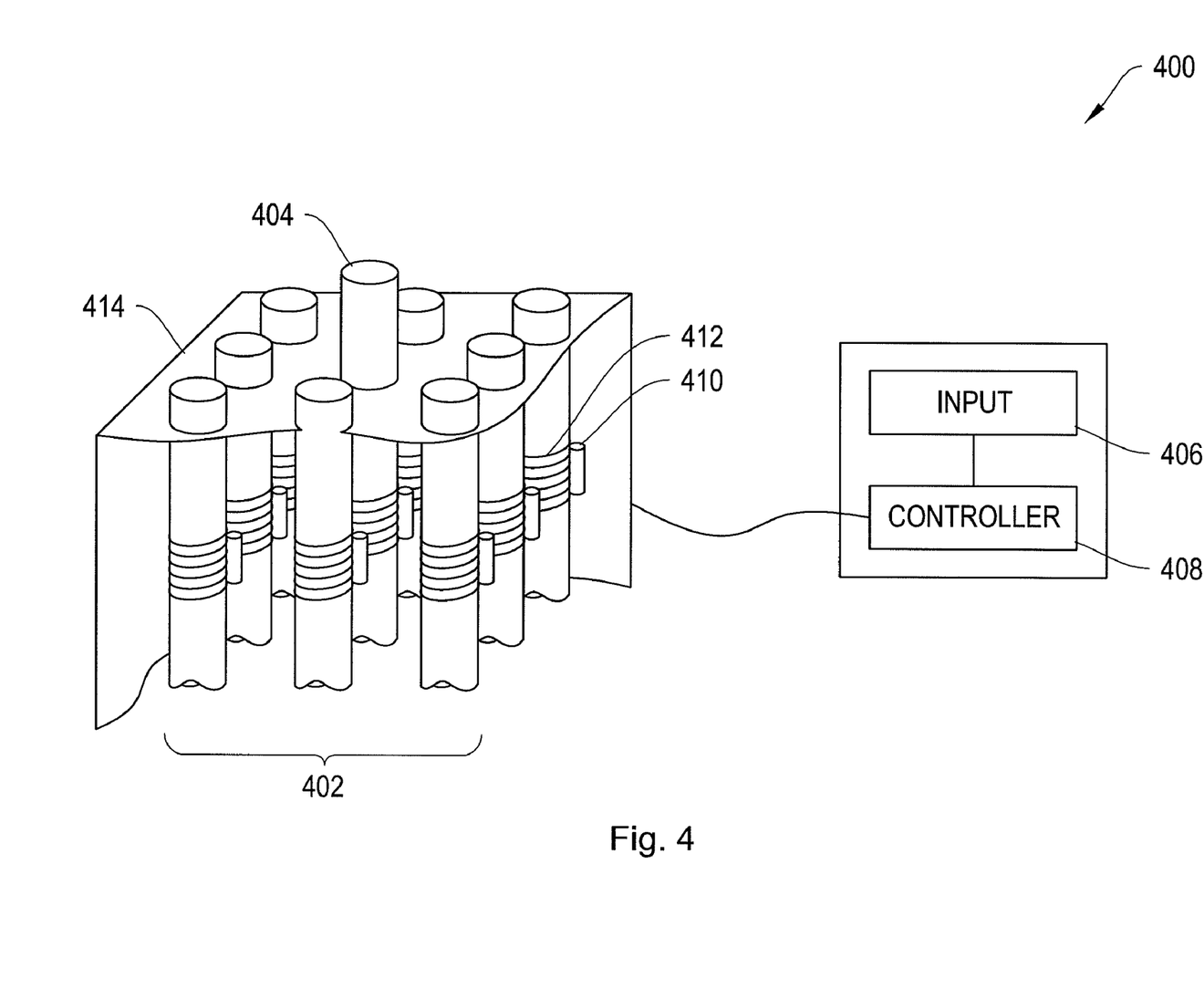
FIG. 4 is an illustrative reference image presentation tool according to an illustrative embodiment of the invention.

FIG. 4 is an example 400 of a reference image presentation tool 206. The tool 400 includes a two-dimensional array 402 of mechanical projections (e.g., 404) which are arranged with respect to a surface 414. The positions of the mechanical projections relative to one another can be rearranged to form a physical relief corresponding to the reference image. Mechanical projection 404 is a pin. In other embodiments, mechanical projection 404 is a cube, a cuboid, a cylinder, a cone, a prism, a pyramid or a tetrahedron. The array 402 generally has one mechanical projection 404 per pixel of resolution of the reference image. For example, the configuration of the mechanical projections of the tool 400 corresponds to a reference image having a simple single bright spot in the center of the patient's field-of-view. The tool 400 also includes an input 406, a controller 408, and a plurality of actuators (e.g., actuator 410). The elements of the tool 400 will be best understood with reference to the method described in FIG. 5.

Figure 5:
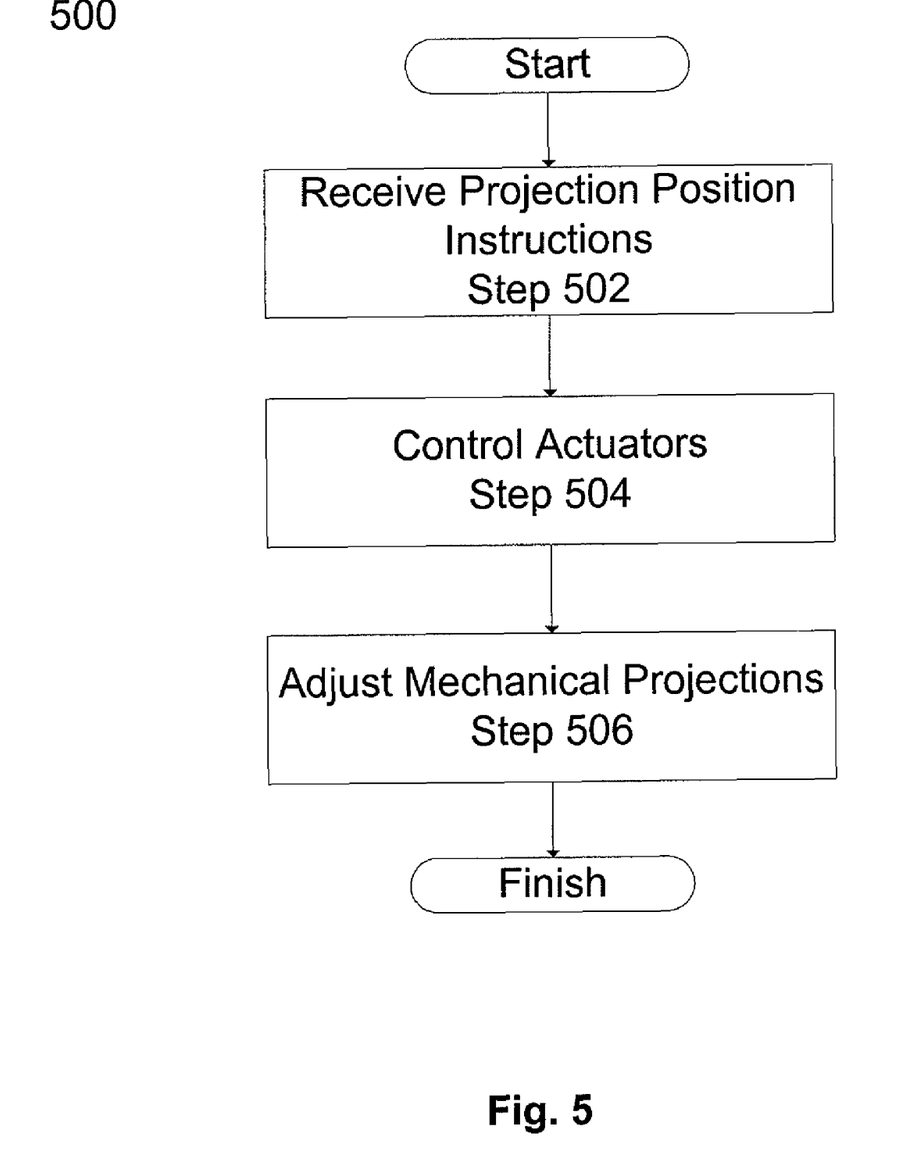
FIG. 5 is a flowchart of a method of using a reference image presentation tool according to an illustrative embodiment of the invention.

FIG. 5 is a flowchart of a method 500 for using the tool 400, according to an illustrative embodiment of the invention. The tool 400 receives projection position instructions (step 502) via the input 406. The projection position instructions include instructions for positioning the array of mechanical projections 402 relative to one another to form a physical relief corresponding to a reference image. The training processor 202 generates projection position information based on the reference image, and transmits the projection position information to the input 406.

Subsequent to receiving projection position instructions, the controller 408 controls the plurality of actuators (e.g., actuator 410) based on the received projection position instructions (step 504). The actuator 410 is a stepper motor that rotates in response to being energized by the controller 408. In other embodiments, the actuator 410 is an electrical motor, a hydraulic piston, a pneumatic actuator, a pneumatic piston, a comb drive, a piezoelectric actuator, a piezoelectric bimorph, or a thermal bimorph. In these embodiments, the controller 408 causes the actuator 410 to move either linearly or rotationally.

The actuator 410 is coupled to the mechanical projection 404 via a gear. The rotation of the actuator 410 causes the gear to rotate, which in turn causes the mechanical projection 404 to move up or down with respect to the surface 414 using the screw thread 412. In other embodiments, the actuator 410 is coupled to the mechanical projection 404 via a plurality of gears, one or more springs, one or more levers, or one or more crankshafts. In some other embodiments, the mechanical projection 404 does not include screw thread 412 (e.g., the mechanical projection 404 includes a smooth surface that allows it to move up and down). The actuator 410 moves the mechanical projection 404 up or down between one of two possible positions, with each position corresponding to a brightness of a corresponding pixel in the reference image. In other embodiments, the actuator 410 moves the mechanical projection 404 between a continuous range of positions, with each position corresponding to a brightness of a corresponding pixel in the reference image. In alternative implementations, the positions of the projections may correspond to other parameters of reference image pixels, including, for example, contrast or color. By moving the mechanical projections 404, the plurality of actuators 410 adjust the array 402 (step 506) to form a physical relief corresponding to the reference image.

Other deformable tools can be similarly employed to provide a tactile stimulus representing the first training reference image. Alternatively, if the patient previously had been sighted, the patient can be informed of the first training reference image verbally. In such embodiments, the tool for non-visually communicating the reference image can be a person, for example a doctor aiding in the training, or an audio speaker connected to a speech synthesizer. In another embodiment, the training system 200 can identify the reference image using Braille text. In still other embodiments, the training system 200 identifies the reference image by presenting it via a presentation tool that includes an array of thermal or electric transducers. Users of the presentation tool can sense levels of an image parameter, including, for example, color, contrast, or brightness, based on the temperature or charge felt from respective transducers in the array.

Referring back to FIGS. 2 and 3, after presenting the reference image to the patient with the tool 400, the training system 200 then trains the implant 100 to correctly induce perception of the reference image (step 310).

Figure 6:
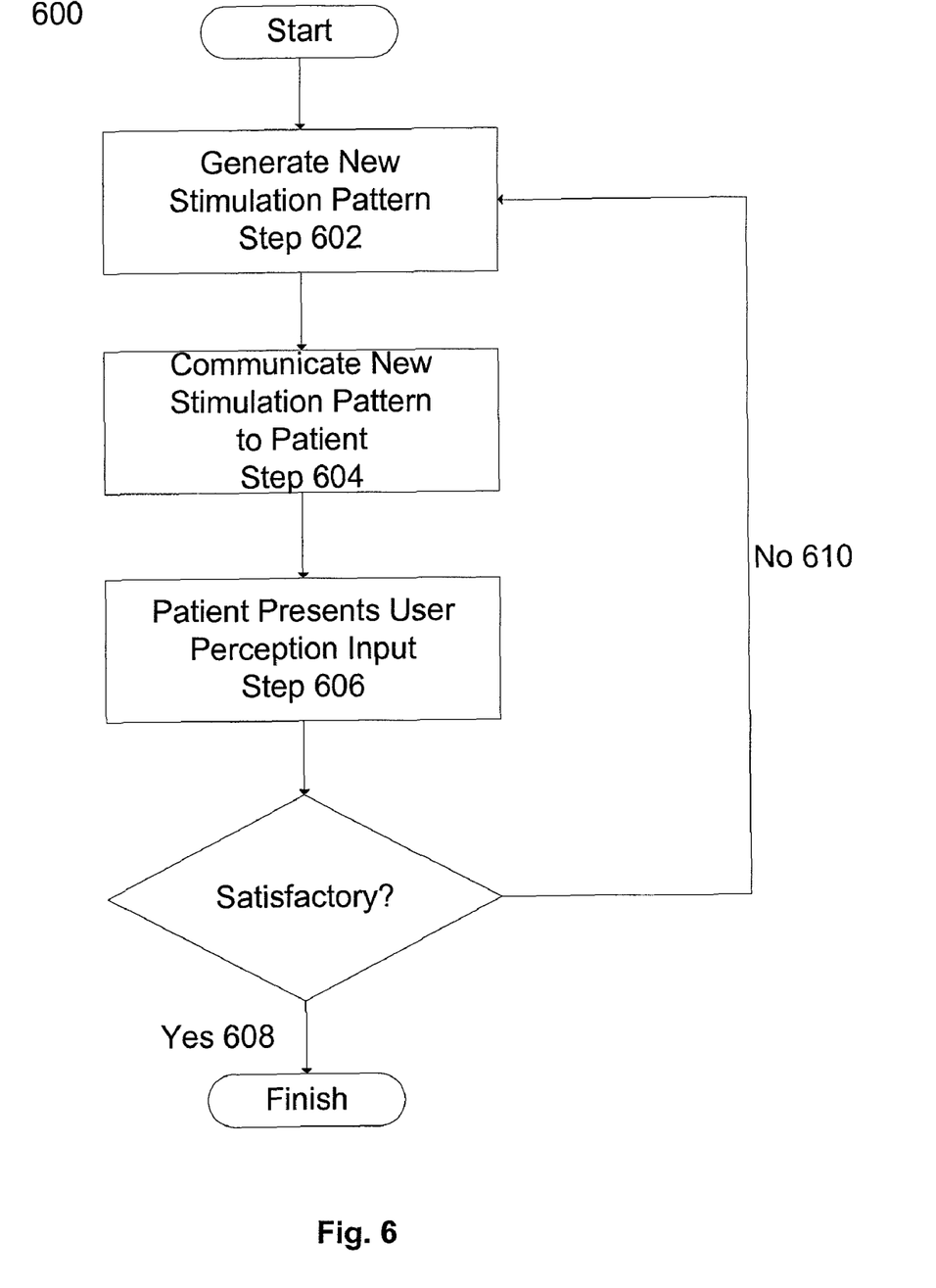
FIG. 6 is a flowchart of a method for generating training data sets for training a retinal implant according to an illustrative embodiment of the invention.

FIG. 6 is a flow chart of a method 600 for training the retinal implant to induce perception of a reference image, according to an illustrative embodiment of the invention. The training processor 202 generates a new stimulation pattern based on a reference image (step 602). The training processor 202 communicates the new stimulation pattern to the patient via the retinal implant (step 604) by transmitting instructions to the electrode array processor 108. The electrode processor 108 energizes the electrodes 104 according to the stimulation pattern, thereby inducing a user perceived image in the patient. The patient, perceiving the results induced by the stimulation pattern, and having an expectation of the induced perception based on the non-visual reference stimulus, presents, using the input tool 204, a user perception input (step 606). The user perception input includes features of the user perceived image.

Figure 7:
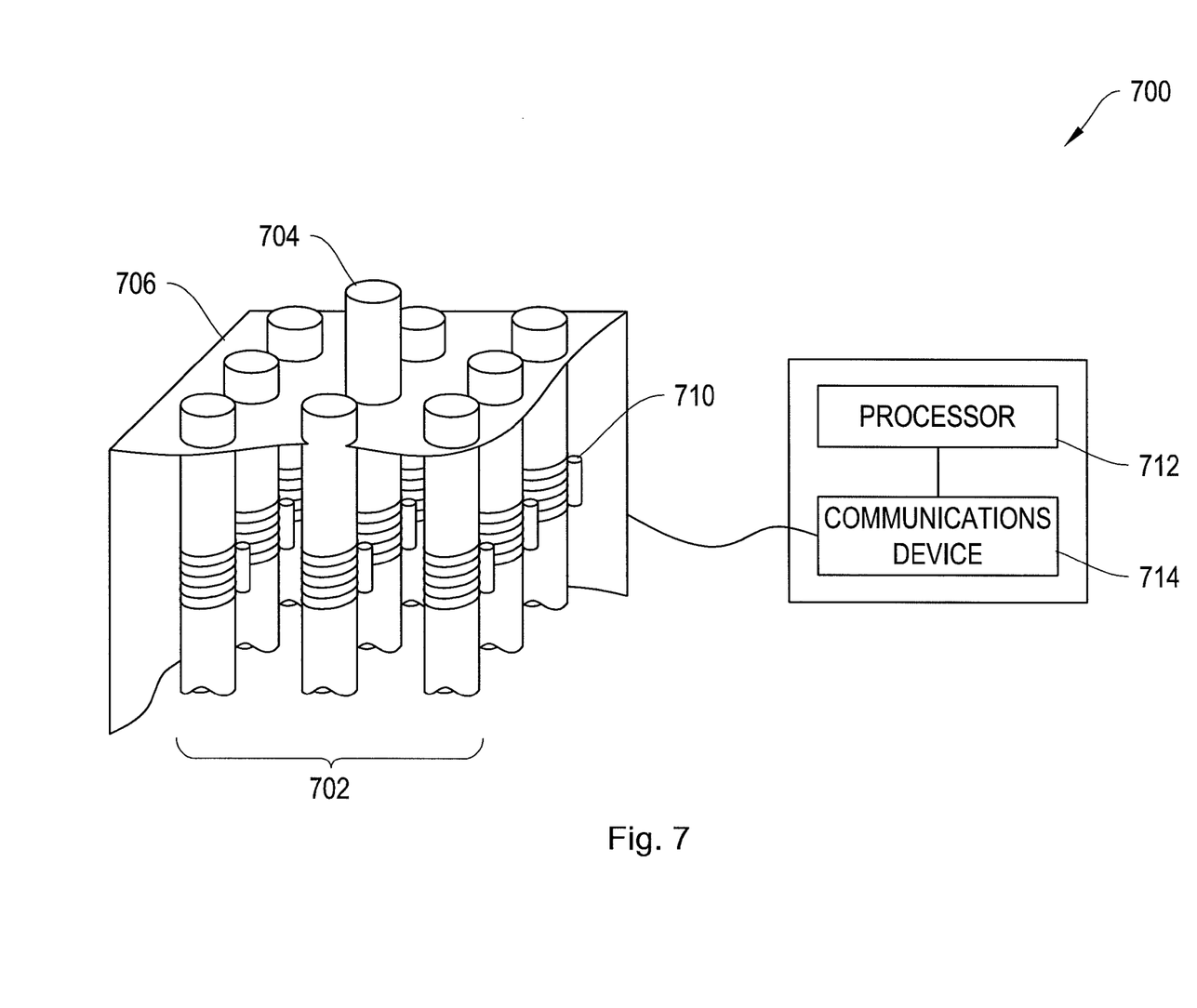
FIG. 7 is an illustrative user input tool according to an illustrative embodiment of the invention.

FIG. 7 is an example 700 of a user input tool 204 for receiving a user perception input. In particular, the user input tool 700 is a user perception input device. The user input tool 700 includes a two-dimensional array 702 of mechanical projections (e.g., 704) arranged with respect to a surface 706.

Each of the mechanical projections in array 702 can be manually moved by a patient to form a physical relief corresponding to a user perceived image. In the illustrative embodiment, mechanical projection 704 is a pin. In other embodiments, mechanical projection 704 is a cube, a cuboid, a cylinder, a cone, a prism, a pyramid or a tetrahedron. The array 702 generally has one mechanical projection 704 to represent each pixel of resolution of the user perceived image. For example, the configuration of the mechanical projections of the user input tool 700 displayed in FIG. 7 corresponds to a user perceived image having a simple single bright spot in the center of the patient's field-of-view. The user input tool 700 also includes a plurality of position sensors (e.g., position sensor 710), a processor 712, and a communication device 714. The elements of the user input tool 700 will be best understood with reference to the method described in FIG. 8.

Figure 8:
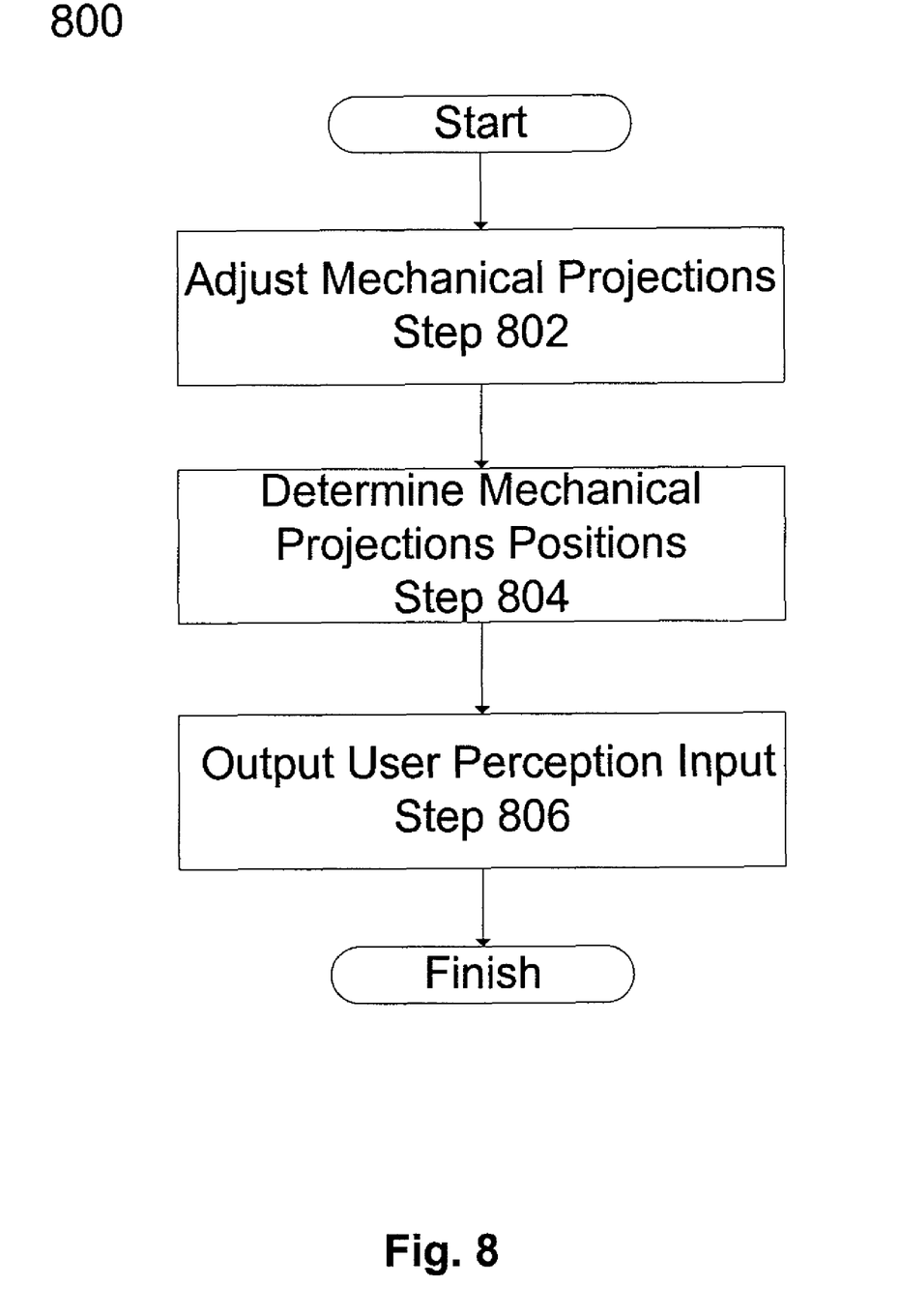
FIG. 8 is a flowchart of a method of using a user input tool according to an illustrative embodiment of the invention.

FIG. 8 is a flowchart of a method 800 for using the user input tool 700, according to an illustrative embodiment of the invention. The patient adjusts the positions of the array 702 with respect to the surface 706 (step 802) to form a physical relief corresponding to a user perceived image. The patient adjusts the position of the mechanical projection 704 by manually moving the mechanical projection 704 up or down. The patient moves the mechanical projection 704 up or down into one of two possible positions, with each position corresponding to a brightness of a corresponding pixel in the user perceived image. In other embodiments, the patient moves the mechanical projection 704 between a continuous range of positions, with each position corresponding to a brightness of a corresponding pixel in the user perceived image. In alternative embodiments, the position of the mechanical projection may correspond to other pixel parameters, including, for example, color or contrast.

After the patient has arranged the mechanical projections 704 in the array 702 to form the physical relief, the plurality of position sensors 710 determine the position of each mechanical projection 704 in array 702 (step 804) relative to the surface 706. Position sensor 710 is a capacitance sensor coupled to the mechanical projection 704 via a wire which determines the displacement of the mechanical projection 704 to determine the position of the mechanical projection 704. In other embodiments, the position sensor 710 is an eddy current sensor, a fiber optic sensor, an inductive sensor, a magnetorestrictive sensor, a photoelectric sensor, or an ultrasound sensor. In all of these embodiments, the position sensor 710 is coupled to the mechanical projection 704 via either a wire or a wireless connection. After determining the position of the mechanical projection 704 with respect to the surface 706, the position sensor 710 transmits the position information to the processor 712. The processor 712 collects position information data as user perception input (step 806). The user perception input includes features of the user perceived image. Processor 712 then transmits the user perception input via the communication device 714 to the training processor 202. The communication device can provide any kind of wired or wireless data communication link, including without limitation, a serial connection, a USB connection, a FIREWIRE connection, an Ethernet connection, a WIFI connection, or a BLUETOOTH connection.

Returning to FIG. 6, based on the user perception input received by the training processor 202 and preferably a fitness function optimization algorithm, the training system 200 generates yet another stimulation pattern (step 602) and communicates the new stimulation pattern to the patient (step 604). The patient subsequently presents another user perception input, once again, based on the induced user perceived image (step 606). This process continues until the patient presents a user perception input that indicates that the generated stimulation pattern induces a visual perception that sufficiently matches the expectations of the patient (step 608).

In practice, no stimulation pattern may generate a perception that identically matches the patient's expected perception of the training reference image. According to one feature, the training processor 202 generates new stimulation patterns until the patient recognizes diminishing returns in each new stimulation pattern.

As indicated above, the generation of each stimulation pattern after the first is based at least in part on a fitness function optimization algorithm. In one embodiment, the fitness function optimization algorithm is a simulated-annealing algorithm. Simulated annealing is a widely used and well-established optimization technique, particularly suited for high-dimensional configuration spaces. The goal of the algorithm is to minimize an energy function, in this case, the subjective evaluation by the blind patient of the difference between the perceived image and the expected perception.

The minimization is performed by randomly changing the value of one or more of the stimulation parameters within physiologically tolerable limits and reevaluating the energy function. Two cases can occur: 1) the change in the variable values results in a new, lower energy function value, i.e. the patient, in response to having his or her visual prosthesis stimulated using the new stimulation pattern, presents a user perception input that more closely matches the reference image than a prior user perception input; or 2) the energy function value is higher or unchanged, i.e. the patient, in response to having his or her visual prosthesis stimulated using the new stimulation pattern, presents a user perception input that is equally close to, or less closely matches the reference image than a prior user perception input. In the first scenario, the new set of parameter values is stored and the change accepted. In the second scenario, the new set of variable values is only stored with a certain likelihood (Boltzmann probability, including an annealing temperature). This ensures that the overall optimization algorithm does not get stuck in local minima of the energy function too easily. The annealing temperature directly influences the Boltzmann probability by making it less likely to accept an energetically unfavorable step, the longer the optimization lasts (cooling schedule). Then, the overall procedure is repeated until the annealing temperature has reached its end value, a preset number of iterations has been exceeded, or a satisfactory vision solution has been attained, i.e., the patient presents a user perception input that matches the reference image within a definable tolerance.

In one embodiment, the training system 200 applies a derivative of the canonical simulated annealing algorithm, by replacing the Boltzmann probability acceptance with an energy threshold acceptance: each configuration with an energy E<Emin+Ethreshold will be automatically accepted, with Ethreshold oscillating between to preset or variable boundaries similar to "simulated reheating and cooling".

In another embodiment, the fitness function optimization algorithm is a genetic algorithm. In general, genetic algorithms try to mimic evolutionary principles used by nature in applying genetic operations such as point mutation, crossover, and inversion to parameter strings, called "genes" or "chromosomes", in order to "evolve" a set of parameters, among a population of parameter sets, by which the algorithm achieves a high fitness as determined by a fitness function (similar to the energy function in simulated annealing). In one embodiment the determination of "genes" or parents for a cross-over operation may be random choice or other schemes for determining the parents for genetic operations, such as cross-over, known to those skilled in the art.

In one such embodiment, the training system 200 uses the following genetic algorithm to generate stimulation patterns. The training system 200 begins with generating a number of stimulation patterns having respective sets of parameters having random values within physiologically tolerable limits. The training system 200 replaces previously generated stimulation patterns with stimulation patterns generated by executing genetic operations on a randomly selected set of the stimulation pattern parameters for each stimulation pattern of a subset or the entire population of stimulation patterns. Based on the subsequent presentation of some or all of the so modified stimulation patterns to the patient, the patient presents user perception inputs for the presented stimulation patterns. Based on the user perception inputs, the genetic algorithm performs a fitness evaluation by comparing the presented user perception inputs to the reference image. In one embodiment, the best performing subset of stimulation patterns moves on into the next generation of stimulation patterns that may be augmented by additional stimulation patterns determined at random so as to maintain a fitness gradient among the stimulation patterns in the population to prevent pre-mature convergence to an average fitness. Other schemes known to those skilled in the art for selecting stimulation patterns to move on from the current generation into the next generation of stimulation patterns may be suitable depending on the specifics of the implemented genetic algorithm.

For the so-formed next generation of stimulation patterns the overall procedure of applying genetic operations to the respective sets of stimulation parameters is repeated until the fitness gradient among the population of stimulation patterns has diminished below a certain threshold (i.e., convergence), a preset number of generations has been exceeded, or a satisfactory vision solution has been attained, i.e., the patient presents at least one user perception input that matches the reference image within a definable tolerance. In another embodiment, the training system 200 uses evolutionary algorithms or evolutionary strategies that follow similar principles used for genetic algorithms or simulated annealing.

In another embodiment, the optimization algorithm operates in the following fashion. The training system 200, after receiving a user perception input from a patient compares the stimulation pattern associated with the user perception input with the last generated stimulation pattern to identify differences in electrode output parameters in the stimulation patterns. In the subsequently generated stimulation pattern, at least one identified difference between the stimulation patterns is further emphasized. For example, if the voltage applied to a particular electrode in the electrode array in the stimulation pattern associated with the user perception input is 5% greater than the voltage applied to that electrode in the last generated stimulation pattern, a subsequent stimulation pattern would apply a voltage to that electrode that is 8% greater than that applied in the last generated stimulation pattern. Such increases in voltage to that electrode in subsequently generated stimulation patterns continue while the patient continues to present user perception inputs that ever more closely resemble the reference image. The increases cease when the patient presents a user perception input that less closely resembles the reference image than a prior user perception input, or the voltage reaches physiologically tolerable limits. Then, a different stimulation parameter is altered in subsequently generated stimulation patterns.

After the training system 200 successfully generates a stimulation pattern that induces the visual perception expected by the patient based on the non-visual reference stimulus, the training system 200 repeats (step 610) the training process 600 with additional training reference images. The training system 200 stores training data sets including the reference image, records of all the stimulation patterns that were generated, the user perception inputs, and the final successful stimulation patterns. In alternative implementations, the training data sets only include the reference images and the final successful stimulation patterns.

In one embodiment, the training system 200 analyzes training sets between training sessions that use different reference images in order to improve (step 312) the fitness function optimization algorithm. An ordered choice of reference images can facilitate this optimization (step 312).

After successful stimulation patterns for one or more training reference images are achieved, the training data set(s) is analyzed off-line (step 304) by, for example, an artificial feed-forward-type multi-layer neural network configured, e.g., using the Error-Backpropagation algorithm; a Hopfield-type Attractor neural network configured with, e.g., the Projection Rule or the Pseudoinverse algorithm; and/or a recurrent neural network trained, e.g., with algorithms such as Real-Time Recurrent Learning algorithm and the Time-Dependent Recurrent Backpropagation algorithm to determine a vision solution. The neural network analysis yields the vision solution, which, in one embodiment, is itself a neural network. The vision solution provides the capability to generate stimulation patterns for correctly inducting perception of the reference images and of images not presented as part of the training by applying the "knowledge" extracted from the analysis of the training data set(s). The resulting vision solution is transferred to the image processor 110.

The fitness function optimization algorithm employed by the training system 200 can further be improved by testing the optimization algorithm on sighted subjects. Instead of communicating a reference stimulus to the sighted subject non-visually, the sighted subject is presented with the reference image along with a potential image that corresponds at least in part to the reference image. As with the training of the retinal implant, the sighted subject gives a user perceived description of the potential image (e.g., by verbally describing the potential image, or by forming a corresponding relief using a user perception input device 700). A next set of images is selected for presentation using the fitness function optimization algorithm, however, the electrical stimulus parameters are substituted with direct visual parameters such as brightness, shape, and contrast. Optimization algorithms are objectively compared by comparing the average number of iteration steps before a presented user perception input suitably resembles the reference image. In another embodiment optimization algorithms are objectively compared by comparing the achieved quality of the respective vision solutions, expressed as respective user perception inputs, in either an absolute form, or in a relative form, i.e., after a fixed number of iterations or operations for all optimization algorithms to be compared.

The invention may be embodied in other specific forms without departing from the spirit or essential characteristics thereof. The forgoing embodiments are therefore to be considered in all respects illustrative, rather than limiting of the invention.

What is claimed:

1. A system for training a visual prosthesis comprising:
   a) a reference image presentation tool;
   b) a fitness function optimization algorithm;
   c) a first processor configured to i) present a non-visual reference stimulus corresponding to a reference image to a user having a visual prosthesis via the reference image presentation tool;

ii) output a series of stimulation patterns to the user to induce corresponding user perceived images; and iii) receive a series of user perception inputs corresponding to the respective user perceived images including features of the respective perceived images, wherein at least one stimulation pattern in the series of stimulation patterns is determined at least in part based on the fitness function optimization algorithm and at least one previously received user perception input in the series of user perception inputs;

d) a user input device for providing the user perception inputs to the first processor; the user input device configured to accept and output the user perception inputs received by the first processor, the user input device comprising:

an array of mechanical projections arranged with respect to a surface, wherein the mechanical projections are configured to be manually movable by a user to form a physical relief corresponding to a perceived image;

a plurality of position sensors coupled to respective mechanical projections for determining the position of each mechanical projection with respect to the surface; and a second processor for receiving position information from the plurality of position sensors and for outputting user perception input based on the received position information.

2. The system of claim 1, wherein the first processor is further configured to present the series of stimulation patterns to the user through one of a retinal implant, an optic nerve implant, a cortical implant, and a lateral geniculate nucleus implant.

3. The system of claim 1, wherein the first processor is further configured to:

present additional non-visual reference stimuli corresponding to reference images to the user via the reference image presentation tool;

output corresponding series of stimulation patterns to the user, wherein each series of stimulation patterns is presented via the visual prosthesis; and receive a corresponding series of user perception inputs for each series of stimulation patterns, wherein at least one stimulation pattern in each series of stimulation patterns is determined at least in part based on the fitness function optimization algorithm and at least one previously received user perception inputs in the series of user perception inputs.

4. The system of claim 1, wherein the first processor is further configured to generate a stimulation pattern in the series of stimulation patterns by comparing a user perception input in the series of user perception inputs to a corresponding reference image.

5. The system of claim 1, wherein the first processor is further configured to utilize a simulated annealing algorithm as the fitness function optimization algorithm.

6. The system of claim 1, wherein the first processor is further configured to utilize a genetic algorithm as the fitness function optimization algorithm.

7. The system of claim 1, wherein the first processor is further configured to utilize an evolutionary algorithm as the fitness function optimization algorithm.

8. The system of claim 1, wherein the first processor is further configured to apply the fitness function optimization algorithm to determine a subsequent stimulation pattern in the series of stimulation patterns.

9. The system of claim 1, wherein the reference image presentation tool comprises a plurality of mechanical projections.

10. The system of claim 9, wherein the reference image includes a plurality of pixels, and wherein the mechanical projections of the reference image presentation tool are configurable to correspond to respective pixels of the reference image.

11. The system of claim 1, wherein the reference image presentation tool comprises an audio output.

12. The system of claim 1, wherein the array of mechanical projections are further configured to be positioned in one of two possible positions and the second processor determines a parameter associated with a pixel of a user perceived image based on the determined position of a corresponding mechanical projection.

13. The system of claim 12, wherein the parameter is a brightness level.

14. The system of claim 1, wherein the array of mechanical projections are further configured to be positioned in a continuous range of positions and the processor determines a parameter associated with a pixel of a user perceived image based on the determined position of a corresponding mechanical projection.

15. The system of claim 14, wherein the parameter is a brightness level.

16. The system of claim 1, wherein the user input device further comprises a third processor for sending user perception inputs to the first processor.

17. The system of claim 1, wherein the processor is further configured to present the series of stimulation patterns to the user through one of a tongue stimulator, a mechanical body stimulator, and an electrical body stimulator.

18. A method for training a visual prosthesis comprising:

presenting a non-visual reference stimulus corresponding to a reference image to a user having a visual prosthesis via a reference image presentation tool;

outputting a series of stimulation patterns to the user to induce corresponding user perceived images; and receiving a series of user perception inputs corresponding to respective user perceived images including features of the respective perceived images, wherein at least one stimulation pattern in the series of stimulation patterns is determined at least in part based on a fitness function optimization algorithm and at least one previously received user perception input in the series of user perception inputs; and wherein receiving a series of user perception inputs comprises:

arranging an array of mechanical projections with respect to a surface, wherein the mechanical projections are configured to be manually movable by a user;

allowing the user to manipulate the mechanical projections to form a physical relief corresponding to a the perceived image;

determining the position of each mechanical projection with respect to the surface subsequent to the manipulation thereof by the user; and outputting a user perception input based on the determined position of each mechanical projection with respect to the surface.

19. The method of claim 18, wherein the visual prosthesis is one of a retinal implant, an optic nerve implant, a cortical implant, and a lateral geniculate nucleus implant.

20. The method of claim 18, wherein the visual prosthesis is one of a tongue stimulator, a mechanical body stimulator, and an electrical body stimulator.

21. The method of claim 18, further comprising:
presenting additional non-visual reference stimuli corresponding to reference images to the user via the reference image presentation tool;
outputting corresponding series of stimulation patterns to the user, wherein each series of stimulation patterns is presented via the visual prosthesis; and
receiving a corresponding series of user perception inputs for each series of stimulation patterns, wherein at least one stimulation pattern in each series of stimulation patterns is determined at least in part based on the fitness function optimization algorithm and at least one previously received user perception input in the series of user perception inputs.

22. The method of claim 18, comprising generating a stimulation pattern in the series of stimulation patterns by comparing a user perception input in the series of user perception inputs to a corresponding reference image.

23. The method of claim 18, comprising utilizing a simulated annealing algorithm as the fitness function optimization algorithm.

24. The method of claim 18, comprising utilizing a genetic algorithm as the fitness function optimization algorithm.

25. The method of claim 18, comprising utilizing an evolutionary algorithm as the fitness function optimization algorithm.

26. The method of claim 18, comprising applying the fitness function optimization algorithm to determine a subsequent stimulation pattern in the series.

27. The method of claim 18, wherein presenting the non-visual reference stimulus corresponding to the reference image via the reference image presentation tool comprises:
determining projection position instructions corresponding to the reference image; and
controlling a plurality of actuators based on the determined projection position instructions to adjust an array of mechanical projections with respect to a surface to form a physical relief corresponding to the reference image.

28. The method of claim 18, wherein allowing the user to manipulate the mechanical projections further comprises allowing the user to position each mechanical projection of the array of mechanical projections in one of two possible positions.

29. The method of claim 28, further comprising determining a parameter associated with a pixel of a user perceived image based on the determined position of a corresponding mechanical projection.

30. The method of claim 29, wherein determining a parameter comprises determining a brightness level.

31. The method of claim 18, wherein allowing the user to manipulate the mechanical projections further comprises allowing the user to position each mechanical projection of the array of mechanical projections in any position in a continuous range of positions.

32. The method of claim 31, further comprising determining a parameter associated with a pixel of a user perceived image based on the determined position of a corresponding mechanical projection.

33. The method of claim 32, wherein determining a parameter comprises determining a brightness level.

34. The method of claim 18, further comprising sending user perception inputs to a processor.

* * * * *

UNITED STATES PATENT AND TRADEMARK OFFICE
CERTIFICATE OF CORRECTION

| | | |
|---|---|---|
| PATENT NO. | : 8,260,428 B2 | Page 1 of 1 |
| APPLICATION NO. | : 12/041203 | |
| DATED | : September 4, 2012 | |
| INVENTOR(S) | : Fink et al. | |

It is certified that error appears in the above-identified patent and that said Letters Patent is hereby corrected as shown below:

At column 1, line numbers 27-31, please delete "The U.S. Government has a paid-up license in this invention and the right in limited circumstances to require the patent owner to license others on reasonable terms as provided for by the terms of Grant No. DE-FG02-06ER64310/T-103506 awarded by DOE.";

At column 1, line numbers 27, please add "This invention was made with government support under Grant No. DE-FG02-06ER64310/T-103506 awarded by DOE. The government has certain rights in the invention." **

Signed and Sealed this

Twenty-third Day of October, 2012

David J. Kappos
*Director of the United States Patent and Trademark Office*